United States Patent [19]

Robertson et al.

[11] 4,324,556

[45] Apr. 13, 1982

[54] PORTABLE COHB ANALYZER

[75] Inventors: Robert F. Robertson, Gaithersburg; Thomas J. Connor, Riverdale; F. Lee Rodkey, Kensington, all of Md.

[73] Assignee: The United States of America as represented by the Secretary of the Navy, Washington, D.C.

[21] Appl. No.: 133,749

[22] Filed: Mar. 25, 1980

[51] Int. Cl.$^3$ .................................................. G01N 33/72
[52] U.S. Cl. ................................. 23/230 B; 23/913; 422/68; 356/40
[58] Field of Search ............... 23/230 B, 913; 422/68, 422/73; 356/34, 40

[56] References Cited

U.S. PATENT DOCUMENTS 3,994,585  11/1976  Frey ....................................... 356/40
4,003,662  1/1977  Retzer et al. ........................... 356/40

OTHER PUBLICATIONS

Collision et al., Clinical Chemistry, vol. 14, #2, pp. 162-171.
Klendshoj et al., 183 Journal of Biological Chemistry, p. 297 (1950).
4,134,678 01001979 Brown et al. 356 40
"Gradwohls' Clinical Laboratory Methods and Diagnosis", Frankel et al., vol. I, The C. V. Mosby Co., St. Louis, MO, 1970.
Commins et al., 22 British Journal of Industrial Medicine 139 (1945).
Small et al., 31 Journal of Applied Physiology, p. 154, 1971.
Rodney et al., Clinical Chemistry, 1388-1393, 1979.

*Primary Examiner*—William F. Smith

[57] ABSTRACT

A portable spectrophotometric apparatus and method therefor for measuring the percentage of carboxyhemoglobin (COHb) in blood. The apparatus comprises a spectrophotometer and wavelength selection filters for testing a reference sample having a hemolizing agent and sodium hyposulfite and a treated blood sample with the hemolizing agent and sodium hyposulfite and providing a two component COHb-Hb system for determining relative absorbance values of the two samples at light wavelengths of 420 nanometers and 432 nanometers, the wavelengths corresponding to respective peak absorbance of the components in the high absorbance Soret region on opposite sides of an isobestic point formed by the intersection of their respective absorbance-wavelength curves. The ratio of the derived relative values is compared against predetermined data to determine the percentage of carboxyhemoglobin in the blood.

18 Claims, 5 Drawing Figures

PORTABLE COHB ANALYZER

BACKGROUND OF THE INVENTION

The present invention relates to apparatus and method for testing blood and more particularly to the determination of the percentage of carboxyhemoglobin in blood.

There continues to be a pressing need for reliable methods for measuring the percentage of carboxyhemoglobin (COHb) in blood outside the laboratory under adverse conditions in the field. Traditional methods such as gas chromatography are too demanding for routine use in such situations and require large, precisely calibrated equipment, which as well as requiring substantial time to perform the testing, is unable to withstand usage in the field, and requires laboratory conditions to maintain calibration.

Additionally, testing performed on unconscious persons or newborn children require that only a small amount of blood be used. Spectrophotometric methods based on absorbance measurements lack the sensitivity necessary for small sample volume and often require extensive testing time.

It is well established in the medical literature that COHb levels as low as 10 percent have been proved to have deleterious effects on human performance. In high carbon monoxide situations such as in fire-fighting procedures where the fire-fighters and victims of the fire are exposed to high carbon monoxide levels, it is important that carbon monoxide levels in the blood be readily established. Such is particularly important aboard a ship where the fire gases can be spread through the ship by the ventilating system and especially where a ship deployed at sea is isolated from extensive medical care facilities.

Prior art spectrophotometric apparatus and methods have proven to be unsatisfactory for this need. It is particularly important that the testing be accomplished with a portable instrument on a very small amount of blood, such as derived from a prick on a finger and that the time for testing be short, preferably two minutes. The method of Commins and Lawther in their published article "A Sensitive Method for Determination of Carboxyhemoglobin in a Finger Prick Sample of Blood" 22 British Journal of Industrial Medicine 139 (1965) requires a supply of oxygen and at least 20 minutes to bubble the oxygen through a blood sample. Additionally, the testing must be conducted at four wavelengths which do not provide the required sensitivity and great care must be taken to prevent air contamination of the samples. The method disclosed in the article of Klendshoj, Feldstein, and Sprague entitled "The Spectrophotometric Determination of Carbon Monoxide" appearing at 183 Journal of Biological Chemistry page 297 (1950) uses light wavelengths of 555 and 480 nanometers with one of the wavelengths being an isobestic point formed by the intersection of the absorbance-wavelength curves of COHb and Hb, provides only one one-hundredth of the desired sensitivity, and requires a relatively larger amount of blood. The article by Small, Radford, Frazier, Rodkey and Collision entitled "A Rapid Method for Simultaneous Measurement of Carboxy and Methemoglobin in Blood" appearing at 31 Journal of Applied Physiology at page 154 (1971) tests the sample at four wavelengths, demands great care to prevent contact with air, is dependent upon the pH of the solution, and is critical to the light wavelengths used. Brown et al U.S. Pat. No. 4,134,678 requires relatively larger amounts of blood for testing and does not lend itself to portable use. Thus, the above methods and apparatus do not lend themselves for use outside of the laboratory and performance by other than highly specially trained personnel or for testing unconscious persons, newborn children, or small animals.

Accordingly it is desirable to provide apparatus for testing the percentage of COHb in blood quickly, using a smaller quantity of blood, at greater sensitivity which can be quickly accomplished with a portable instrument outside the laboratory under adverse conditions by para-medical personnel. It is further desirable to provide spectrophotometric apparatus for testing COHb in blood at wavelengths wherein the absorbance of the components are maximized.

It is important that the calibration of such a portable instrument subject to rough handling be minimized. Accordingly it is desirable to minimize calibration requirements and to ascertain the desired values by comparison to predetermined data obtained from high accuracy laboratory equipment.

OBJECTS OF THE INVENTION

Accordingly, it is an object of the present invention to provide for quickly testing the percentage of COHb in a small quantity of blood and with great sensitivity.

It is another object of the present invention to provide for measuring the percentage of COHb in blood outside the laboratory under adverse conditions by para-medical personnel.

Yet another object of the present invention is to provide a spectrophotometer for testing for the percentage of COHb in blood at the wavelengths of 420 nm and 432 nm which permits maximum absorption sensitivity to the blood components measured.

A further object of the present invention is to provide COHb measuring means using a two component system wherein a first test sample is measured at two wavelengths as a reference, the components of the blood sample are measured at the two wavelengths and the derived values are manipulated to determine the percentage measurement.

Still another object of the present invention is to provide COHb measuring means at peak absorbance wavelengths on opposite sides of an isobestic thus amplifying the difference of the relative absorbance values to increase the sensitivity and speed of the test procedure and reduce the quantity of blood needed for performing the test.

Other objects, advantages, and novel features of the present invention will occur to those skilled in the art as the following detailed description of the invention proceeds.

SUMMARY OF THE INVENTION

A first sample comprising deionized water with a buffering agent and a reducing agent, i.e. sodium hyposulfite, is prepared and serves as a reference sample. A second sample is prepared and comprises the ingredients of the first sample along with a sample of the blood under test. The reducing agent chosen does not affect the carboxyhemoglobin but reduces all other hemoglobin present to deoxyhemoglobin (Hb) thus effectuating a two-component system. Spectrophotometric analysis is performed on the two samples at wavelengths of 420 nm and 432 nm chosen to maximize the absorption difference of the two components for greater sensitivity in a manner such that the criticality of wavelength changes is reduced. The relative absorbance values of the two samples at the two wavelengths is manipulated and compared to predetermined data derived from finely tuned laboratory equipment for determining the percentage of carboxyhemoglobin in the blood sample. Thus, the test can be performed in a non-critical but sensitive manner in the field with a portable instrument by para-medical trained personnel.

BRIEF DESCRIPTION OF THE DRAWINGS

For a better understanding of the present invention, reference may be had to the accompanying drawings wherein the same reference numerals have been applied to like parts and wherein.

DETAILED DESCRIPTION OF THE PREFERRED EMBODIMENT

The analytical basis for the spectrophotographic instrument of the present invention has been developed mathematically from the Beers-Lambert Law of absorption which defines the photometric relationships in measuring the concentration of a colored compound. In particular, the absorbance of each component in a mixture is proportional to its concentration. At a given wavelength and at a fixed pathlength L in cm, the intensity I of the light transmitted through the solution decreases logarithmically with increasing concentration. This can be written in terms of the absorbance "A" as $$\log_{10}\left(\frac{I_o}{I}\right) = \epsilon L C = A$$

where C is the concentration in mol Liter, and $\epsilon$ is the molar absorption coefficient.

In the present invention, the absorbance is measured at wavelengths of 420 nm and 432 nm and the absorbance at each wavelength is as follows:

$$A_{420} = (\epsilon_{420}^{Hb}(1-x) + \epsilon_{420}^{COHb}x)LC$$

$$A_{432} = (\epsilon_{432}^{Hb}(1-x) + \epsilon_{432}^{COHb}x)LC$$

where x represents the fraction of the total hemoglobin present as COHb with the remainder present as Hb with no other absorbing species present. The simultaneous solution of these equations gives the fraction of total hemoglobin present as COHb by:

$$x = \frac{A_{432}\epsilon_{420}^{Hb} - A_{420}\epsilon_{432}^{Hb}}{A_{420}(\epsilon_{432}^{COHb} - \epsilon_{432}^{Hb}) - A_{432}(\epsilon_{420}^{COHb} - \epsilon_{420}^{Hb})}$$

Figure 1:
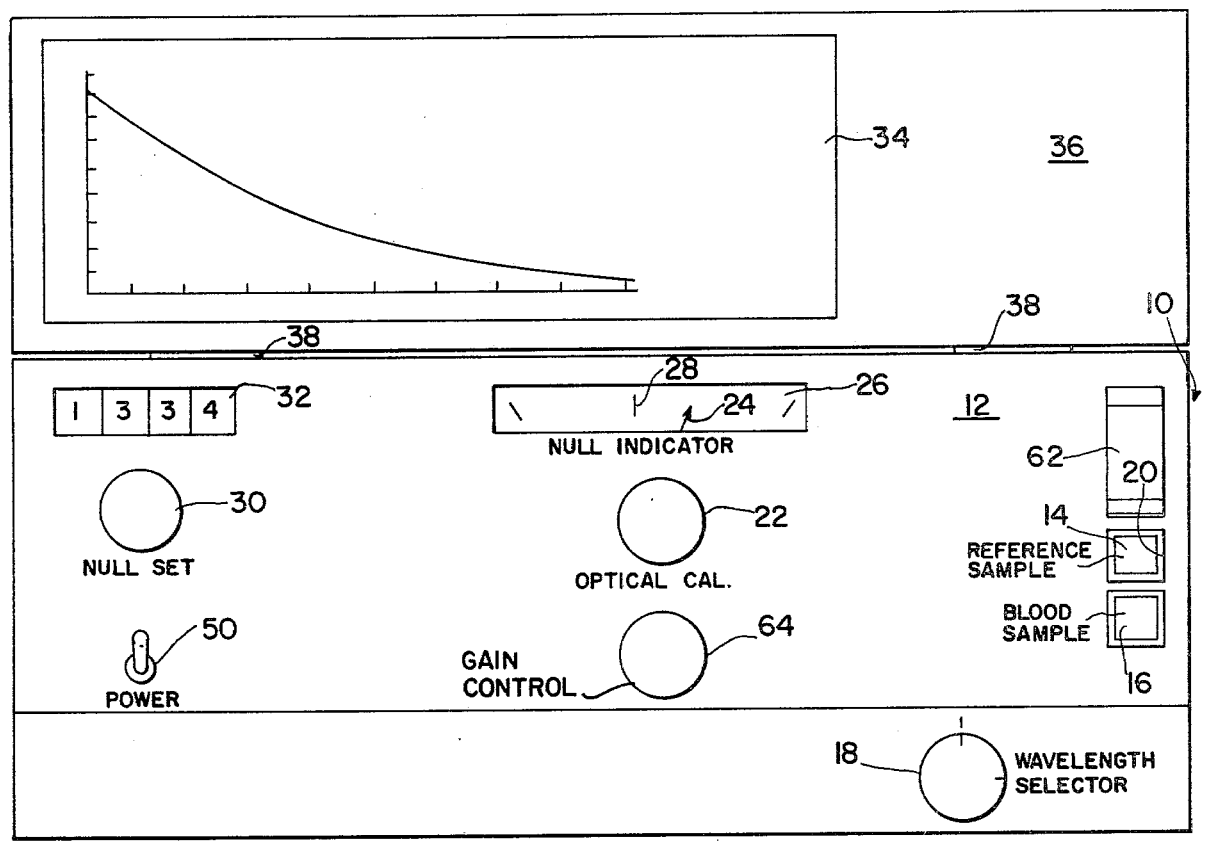
FIG. 1 is an oblique isometric view of an embodiment of the present invention.
Figure 2:
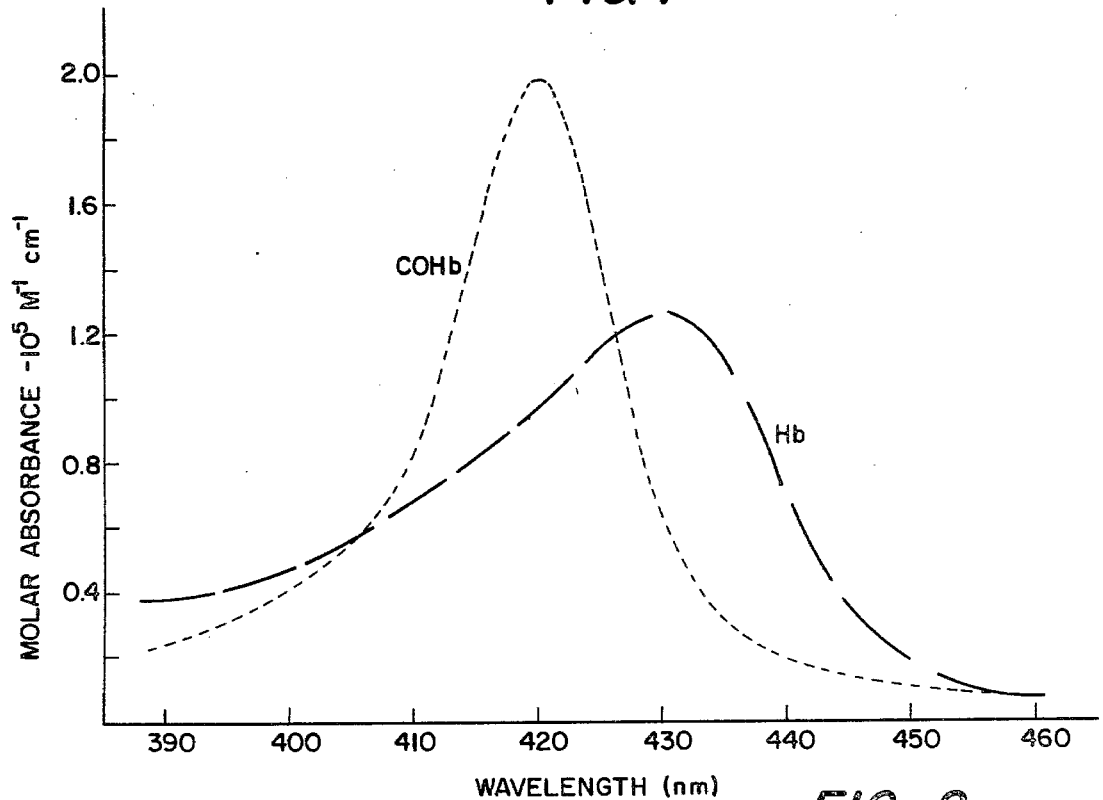
FIG. 2 is a graph showing the absorption of carboxyhemoglobin and hemoglobin vs. wavelength in the Soret region.

Referring now to the drawings wherein like reference characters have been applied, there is shown in FIG. 1 a test apparatus for determining the percentage of COHb in blood, generally designated 10, and incorporating the apparatus of the present invention. Within an enclosure 12 thereof are disposed areas for a reference test sample 14 and a blood test sample 16 which are both prepared in a manner to be described hereinafter and a spectrophotometer (shown in the block diagram flow chart of FIG. 5) for light illumination and testing the samples 14 and 16. The testing is performed in the Soret region where the absorbance of the blood components of interest, i.e. carboxyhemoglobin (COHb) and deoxyhemoglobin (Hb), have very high absorbance, the respective absorbance curves being shown in FIG. 2. As shown on the curves of FIG. 2, the absorbance of COHb is nearly double that of Hb at 420 nm while the absorbance of Hb is nearly three times that of COHb at 432 nm. Additionally the test wavelengths of 420 nanometers (nm) and 432 nm are peaks of the two blood components of interest and are on opposite sides of the cross-over or isobestic point such that the difference between the absorbance values at the respective wavelengths of the respective blood components are further maximized due to the amplification effect of being on opposite sides of the isobestic point. Thus, the chosen wavelengths permit not only testing of the respective components at a peak of their absorbance but additionally maximize the difference between their absorbance values thereby greatly increasing the sensitivity of the measurement.

The light wavelengths are selected by interference filters which are selected by wavelength selector 18. Interference filters were chosen because they will never go out of frequency calibration, and if deterioration does occur only the intensity of the transmitted light will change which can be compensated for by a gain control as disclosed hereinafter. The light is passed through the test samples 14, 16 within receptacle 20 and is detected by photodetectors 54 (FIG. 5) with the electrical signal generated being operated upon by the spectrophotometer circuitry. Initially, two identical samples 14 are inserted into receptacle 20 and any difference of readings between the two samples 14 is nulled out by manipulation of the optical calibrate control 22 until the pointer 24 of the null indicator meter 26 indicates null at center position 28. This initial nulling operation is performed to remove from the measurement any differences within the instrument which might affect the measurement. The second reference sample 14 is then replaced by blood sample 16. Since the sample 16 which includes the blood under test has a different absorbance than the reference sample 14, the null indicator 26 will again show an off-center or non-null reading. The null indicator 26 is then reset to the null point 28 by turning the null set control 30 which is coupled to a calibrated vernier indicator 32 which indicates a first relative numerical value of the absorbance of the sample of blood at the respective wavelength. Thus, the first relative value is the increased absorbance of the blood sample 16 above the relative absorbance value of the reference sample 14.

The wavelength selector 18 is then rotated for selecting the wavelength filter for 432 nm and the above test procedure including optical calibration is again performed at this new wavelength and a second relative numerical value of absorbance of the sample of blood is obtained.

The ratio between the second relative value and the first relative value is obtained by dividing the second value by the first value. This division can be accomplished with pencil and paper, with a slide rule, digital calculator, or in a programmable digital manner as will be described hereinafter.

Figure 4:
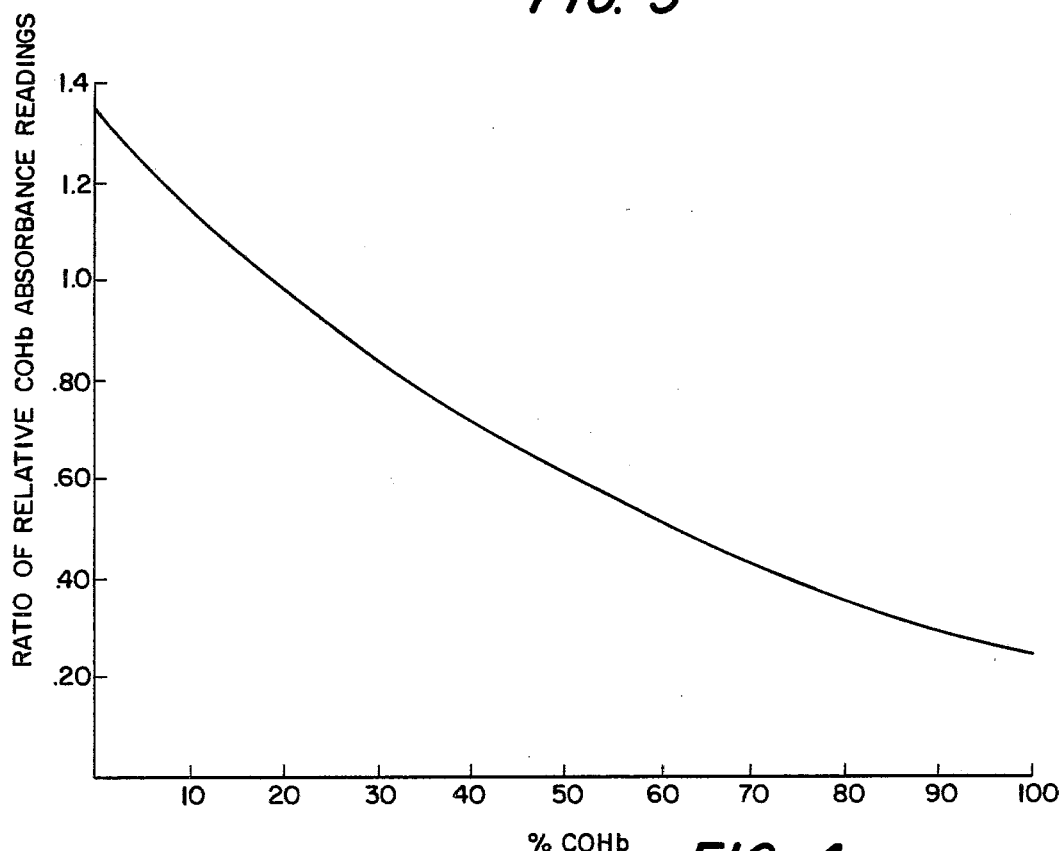
FIG. 4 is a graph relating relative absorption ratios determined by the present invention to percentage of carboxyhemoglobin in the blood.

Referring now to FIG. 4, there is shown a graph of the ratio of relative COHb absorbance readings to the percent COHb in the blood. The ratio of the relative absorbance values appears along the ordinate axis of the graph of FIG. 4 with the percentage of COHb in the blood being the abscissa axis. Thus, once the ratio of the relative absorbance values is determined, the percentage of COHb is then known. The ratio can also be determined by dividing the first relative value by the second relative value with the graph of FIG. 4 being appropriately revised. The graph of FIG. 4 has been previously determined in a laboratory using a gas chromagraph or other suitable laboratory precision equipment which is too bulky and delicate for transportation into the field. The laboratory procedure for determining this graph is disclosed in the paper entitled "Determination of Carbon Monoxide in Blood by Gas Chromatography" by Collison, Rodkey and O'Neal appearing in 14 Clinical Chemistry 162 (1968) and the paper entitled "Spectrophotometric Measurement of Carboxyhemoglobin and Methemoglobin in Blood" by Rodkey, Hill, Pitts and Robertson appearing in 25 Clinical Chemistry 1388 (August 1979). A replica of graph 34 of the graph of FIG. 4 is disposed on the cover 36 which is pivotably supported to enclosure 12 by hinges 38. In this manner, the portable instrument is calibrated against the lab instrument and all other points on the graph become constants.

Figure 3:
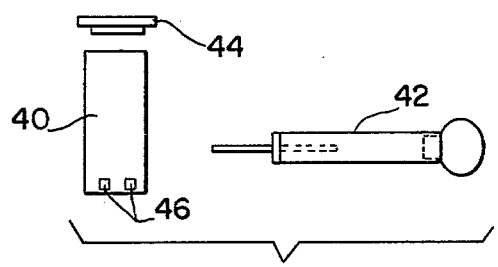
FIG. 3 is a front elevational view of implements used with the present invention.

More particularly, the two reference samples 14 and the blood sample 16 are prepared at the same time. Due to the great sensitivity of the present invention, only three microliters of blood, the amount available from a finger pin prick, is required. Three disposable cuvettes 40, (FIG. 3) are simultaneously prepared. A standard test solution for providing a test reference is simultaneously prepared for each cuvette having a capacity of five milliliters to assure that the same concentration appears in each cuvette. The standard test solution, which also serves as a carrier solution, includes a reducing agent and a tris diluent in deionized water. The tris diluent is of 0.01 mol/liter (0.0121%) concentration and provides a pH buffer and a hemolyzing medium for the blood. The reducing agent comprises a sufficient quantity, typically 2 milligrams per milliliter (0.2%), of sodium hydrosulfite ($Na_2S_2O_4$) to reduce all of the other hemoglobin in the blood sample to deoxyhemoglobin (Hb) but having no effect on the carboxyhemoglobin (COHb) present, and to remove all oxygen from the mixed solution including oxygen which may inadvertently be added to the solution during handling thereby making the handling of the solution non-critical whereas the prior art requires great care to prevent oxygen contamination.

The three microliters of blood is removed from the finger by a calibrated capillary tube 42 (FIG. 3) having a total capacity equal to the desired amount of blood desired to be drawn up for the test. The blood sample is then deposited into one of the cuvettes having the carrier solution comprising the hemolizing agent and the reducing reagent, the cover 44 is applied to all cuvettes and the contents are mixed. The cuvettes 40 are each provided with mixer beads 46 for assuring adequate mixing of the solutions.

Figure 5:
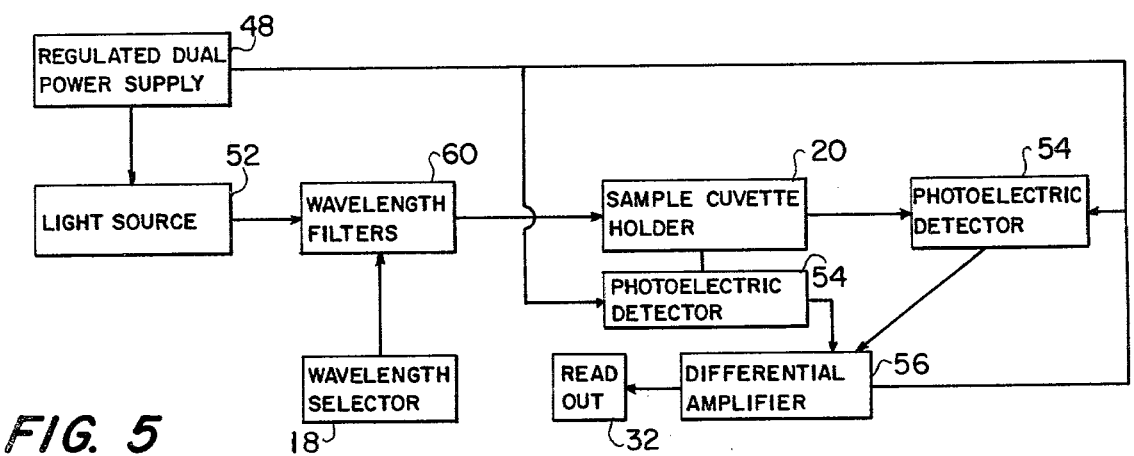
FIG. 5 is a block diagram flow chart of the spectrophotometer of the present invention.

Referring now to FIG. 5, there is shown a block diagram flow chart of the spectrophotometer of the present invention. A regulated dual power supply 48 powers the instrument and is powerable in a portable mode by six battery "D" cells and is alternately powerable where an appropriate AC power source is available. The power supply is turned on by a panel power switch 50 (FIG. 1) and power is supplied to the appropriate members, e.g. a light source 52, photoelectric detectors 54, differential amplifier 56 and if necessary, read-out 32.

The light source 52 is a tungsten filament bulb operable at the power supply voltage. The light from the light source 52 is passed through wavelength filters 60 which are singly selectable from the front panel by wavelength selector 18. The wavelength filters 60 are interference filters mounted on a movable mount such as a wheel which in the present embodiment is mechanically coupled to the knob of selector 18 but it is within the contemplation of the present invention that the wavelength filters 60 can be electrically selectable by electronic means operating a solenoid or servo motor by means discussed hereinafter. The wavelength filters select a bandpass of light wavelength emitted from the lamp source 52 for illuminating the test samples 14, 16. Any deterioration with time of the interference filters only affects the intensity of the light transmitted by the filters rather than the wavelength of the light transmitted as is common with slit or grating filters thereby assuring measurement at the selected optimum frequencies.

The cuvettes for examples 14, 16 are disposed within the cuvette holder 20 which is provided with a cover 62 (FIG. 1) placeable over the holder 20 while the testing is being conducted. The light through the respective cuvettes is sensed by the respective photoelectric detectors 54 for providing an electrical output related to the light intensity.

Laboratory spectrophotometers commonly have light detectors comprising photoamplifier tubes or the like which are bulky and require high voltage power supplies as well as associated amplifiers. For portability, the spectrophotometer of the present invention uses matched blue-sensitive cadmium sulfide photocells as photodetectors.

The output from the photodetectors 54 is fed to a solid state differential amplifier 56. Differential amplifier 56 comprises independent amplifiers associated with the respective photodetectors and an output means proportional to the difference between the two inputs so that when the two inputs from the photodetectors 54 are equal in amplitude, the output means indicates zero. The null set control 30 is a calibrated potentiometer connected to vary the gain of the portion of the differential amplifier 56 associated with the photoelectric detector 54 measuring the light intensity of the reference sample and the optical calibrate is a potentiometer varying the gain of the portion of the differential amplifier 56 associated with the photoelectric detector 54 sensitive to the light transmitted through the blood sample 16. The null indicator 26 is a meter movement having both plus and minus deflection capability with a quiescent position of the pointer 24 at midpoint 28. For such an indicator, at a zero output from the differential amplifier 56, the null indicator pointer 24 will be at the mid-point indication. When the null set control 30 is adjusted to the null position 28 as indicated by the null indicator 26, the calibrated vernier read out 32 will indicate a relative value of the voltage gain change necessary to bring the output of the independent amplifier for the reference sample to the same level as that the blood sample amplifier since the reference sample photodetector 54 will receive more light because of the increased density of the blood sample and consequently will have higher output than the amplifier portion related to the photoelectric detector 54 for the blood sample. Accordingly, to achieve null, the output of the reference amplifier is reduced by adjustment of the null set control 30.

A gain control 64 is adjustable from the front panel 12 and is a variable resistor connected in series with the null indicator meter 26 for adjusting the full scale sensitivity of the null indicator. Thus, if the test samples 14, 16 are darker or the wavelength selection filters have deteriorated thereby reducing the intensity of light transmitted therethrough, these changes can be compensated for by adjustment of the gain control 64. Thus, the blood test sample must only be diluted enough to get sufficient light through and is not quantitative dependent. The gain control 64 can be effectuated many ways and it is within the contemplation of the present invention that adjustment of the quantity of light reaching the test samples, as e.g. by a variable width slit or a variable density shade interposed in the light path, could serve as a gain control.

It is further within the contemplation of the present invention that the testing of the reference sample and the blood sample 14, 16 can be accomplished in a preprogrammed electrical manner using digital circuitry. For example, in such a case, a programmable microcomputer along with an Arithmetic Logic Unit (ALU), Random Access Memory (RAM), Read Only Memory (ROM) and associated clock and interface circuits could be used. The microcomputer, accordingly programmed, would choose a first light wavelength of 420 nm the selection of which would be accomplished with a solenoid or servo control motor operating a mechanical device such as a wheel or the like for placing the selected wavelength filter in place in the light path. The values of light absorbance of the reference sample $A_1$ and the blood containing samples $B_1$ are then fed to an analog to digital converter (A/D converter) and the respective digital absorbance values are stored in the RAM memory. The value of $A_1$ is then subtracted from the value of $B_1$ with the result $C_1$ being the relative value of light absorbance by the blood components at the first wavelength being stored in the RAM memory.

Further according to the programming of the microcomputer, the second light wavelength filter is put in place as described above and the second relative absorbance values $A_2$ and $B_2$ detected by the photodetectors are converted into digital values and stored in the RAM memory with the value $A_2$ being subtracted from $B_2$ to determine the result $C_2$ which is the relative value of light absorbance by the blood components at the second wavelength of 432 nm which is stored in the RAM memory.

The ratio R of $C_2$ to $C_1$ is then formed by dividing $C_2$ by $C_1$ in the ALU using a suitable division algorithm with the quotient, the ratio R, being stored in the RAM Memory.

The ROM is preprogrammed and provides a look-up table of the graph of FIG. 4. The value of R previously determined is then compared with values of one of the ordinates of the graph with the look-up table providing the value of percent of COHb in the blood which is then read out and placed in the RAM memory. This determined value of percentage of COHb is then fed to a decoder connected to a digital panel readout for direct numerical display of the percentage of COHb in the blood sample. Examples of such digital electronic circuitry for analysis of blood components may be found in U.S. Pat. No. 4,134,678 to Brown et al.

Thus there is provided an apparatus and method therefor for measuring the percentage of carboxyhemoglobin in blood which permits rapid determination of percentage of COHb in blood from a small quantity of blood at great sensitivity. The sample of blood is reduced to a two-component system and spectophotometrically analyzed relative to a reference sample at 420 nm and 432 nm which are the peak absorbance wavelengths of the two blood components on opposite sides of an isobestic point to derive relative absorbance values. The percentage of COHb is then determined by comparing the ratio of the derived relative absorbance values against predetermined data ascertained in the laboratory by highly calibrated and sensitive laboratory instruments.

Many modifications and variations of the present invention will occur to those skilled in the art. It is therefore to be understood that within the scope of the appended claims the invention may be practiced otherwise than specifically described above.

What is claimed is:

1. An apparatus for determining the percentage of carboxyhemoglobin in blood comprising:
   a spectrophotometer operable at preselected light wavelengths for determining relative light absorption values for each of a test sample and a reference sample at each of said preselected light wavelengths;
   means for selecting first and second respective wavelengths of substantially 420 nanometers and 432 nanometers of operation of said spectrophotometer;
   means for testing said samples at said first and second wavelengths, the reference sample comprising a mixture of a liquid carrier and a reducing reagent, the test sample comprising a mixture of the liquid carrier, the reducing reagent, and a sample of blood under test; and
   means for determining the percentage of carboxyhemoglobin in said blood from the ratio of said relative light absorption values.

2. The apparatus of claim 1 wherein the reducing reagent comprises sodium hyposulfite.

3. The apparatus of claim 2 wherein said liquid carrier comprises deionized water and a hemolyzing medium with a pH buffer.

4. The apparatus of claim 1 wherein said wavelength selection means comprises a plurality of interference filters, the filters being sequentially selectable.

5. The apparatus of claim 1 wherein said determining means comprises means for determining relative absorption values of the second test sample at the first and second wavelengths with respect to relative absorption values of the first test sample at the respective wavelengths and determining the ratio of the relative absorption values of the second test sample.

6. The apparatus of claim 5 wherein said determining means further comprises means for determining the percentage of carboxyhemoglobin in the blood from the comparison of the determined ratio against predetermined data.

7. The apparatus of claim 5 wherein the apparatus comprises a power supply, a light source powered by the power supply, wavelength filters for selecting light wavelengths emitted by the light source, a wavelength selector for selecting the wavelengths filters, a cuvette holder for holding cuvettes containing specimens under test, photoelectric detectors for detecting the light values transmitted through different portions of the cuvette holder, a differential amplifier powered by the power supply for determining the difference between light values detected by the respective photoelectric detectors, and read out means of the difference between light values.

8. A method for determining the percentage of carboxyhemoglobin in blood comprising the steps of:
preparing a reference and a test samples, the first reference sample comprising a mixture of a liquid carrier and a reducing reagent, the test sample comprising a mixture of the liquid carrier, the reducing reagent, and a sample of blood under test, testing said samples at a first and a second respective light wavelength of substantially 420 nanometers and 432 nanometers and determining the relative light absorption values of each of the samples at each of the first and second light wavelengths; and
determining the percentage of carboxyhemoglobin in the blood from the ratio of derived relative absorption values.

9. The method of claim 8 wherein the reducing reagent is sodium hyposulfite.

10. The method of claim 8 wherein the liquid carrier consists essentially of dionized water and a hemolyzing medium with a pH buffer.

11. The method of claim 8 wherein the step of determining of percentage comprises determining the relative absorption values of the second test sample at the first and second wavelengths with respect to the relative absorption values of the first test sample at the respective wavelengths and determining the ratio of the relative absorption values of the second test sample.

12. The method of claim 8 wherein the step of determining further comprises determining the percentage of carboxyhemoglobin in the blood from the comparison of the determined ratio against predetermined data.

13. A method of determining the percentage of carboxyhemoglobin in blood comprising the steps of:
preparing a test sample and a reference sample, the test sample comprising a mixture of a liquid carrier and a reducing agent which acts to reduce all hemoglobin in blood except COHb to deoxyhemoglobin (Hb), the test sample comprising the same mixture as the test sample plus a desired quantity of the blood to be tested;
exposing the reference and test samples to light of a frequency at which the absorbance of COHb is a maximum, determining the light absorption values of the two samples and using these values to obtain a relative light absorption value at this frequency;
exposing the two samples to light of a frequency at which the absorbance of Hb is a maximum, determining the light absorption values of the two samples and using these values to obtain a relative light absorption value at this frequency;
obtaining the ratio of the relative light absorption values; and
comparing this ratio to a known graph of relative light absorption values vs. percentage of COHb to obtain the percentage of COHb in the blood under test.

14. A method as in claim 13 wherein:
the two light absorption values of each sample are subtracted from each other to obtain the relative absorption value for that sample.

15. An apparatus for determining the percentage of carboxyhemoglobin (COHb) in blood comprising:
means for producing electromagnetic wave outputs at two preselected wavelengths and for determining the relative light absorption values for each of a test sample and a reference sample at each of said preselected wavelengths, said preselected wavelengths being, respectively, a peak absorption wavelength for deoxyhemoglobin (Hb) and a peak absorption wavelength for COHb,
said test sample comprising a small quantity of blood and a liquid combination for reducing all hemoglobin therein, except COHb, to Hb, and said reference sample comprising only a quantity of said liquid combination;
means for exposing said test and reference samples to one of said waves at one of said preselected wave frequencies, measuring the absorption of each sample, and obtaining a relative absorption value therefrom, and for exposing the samples to the second frequency wave, measuring the absorption of each sample, and obtaining a second relative absorption value therefrom;
means for determining the ratio of the relative absorption values; and
means for determining the percentage of COHb in the tested blood by comparing the determined ratio to a indicator of the percentages of COHb in terms of relative ratio values.

16. An apparatus as in claim 15, wherein:
said frequencies are light frequencies at approximately 420 and 432 nanometers, respectively.

17. An apparatus as in claim 15, wherein:
said liquid combination comprises tris diluent and sodium hydrosulfite.

18. An apparatus as in claim 15, wherein:
the amount of blood taken for said test sample is no more than 3 microliters.

* * * * *